United States Patent
Stone

(10) Patent No.: US 8,425,954 B2
(45) Date of Patent: Apr. 23, 2013

(54) CANNA AND SHEA TOPICAL CREAM

(76) Inventor: Sonya Stone, San Francisco, CA (US)

( * ) Notice: Subject to any disclaimer, the term of this patent is extended or adjusted under 35 U.S.C. 154(b) by 83 days.

(21) Appl. No.: 13/192,442

(22) Filed: Jul. 27, 2011

(65) Prior Publication Data

US 2012/0027701 A1 Feb. 2, 2012

Related U.S. Application Data

(60) Provisional application No. 61/368,163, filed on Jul. 27, 2010.

(51) Int. Cl.
*A61K 36/18* (2006.01)
*A61P 29/00* (2006.01)

(52) U.S. Cl.
USPC ............. 424/774; 424/59; 424/725; 424/778; 514/969

(58) Field of Classification Search .................... 424/725
See application file for complete search history.

(56) References Cited

U.S. PATENT DOCUMENTS

2007/0280898 A1 * 12/2007 Riddle ............................ 424/74

* cited by examiner

*Primary Examiner* — Walter Webb
(74) *Attorney, Agent, or Firm* — Steven A. Nielsen; Allman & Nielsen, P.C. NielsenPatents.com

(57) ABSTRACT

A THC composition comprises cannabis leaves simmered in butter, which is then filtered and cooled, and then mixed with shea butter. The resulting compound is used for topical skin relief, sun protection for skin and other uses. The butter used for simmering the cannabis leaves may be cow butter, sheep butter, olive oil, cooking oil, and other compositions.

8 Claims, 1 Drawing Sheet

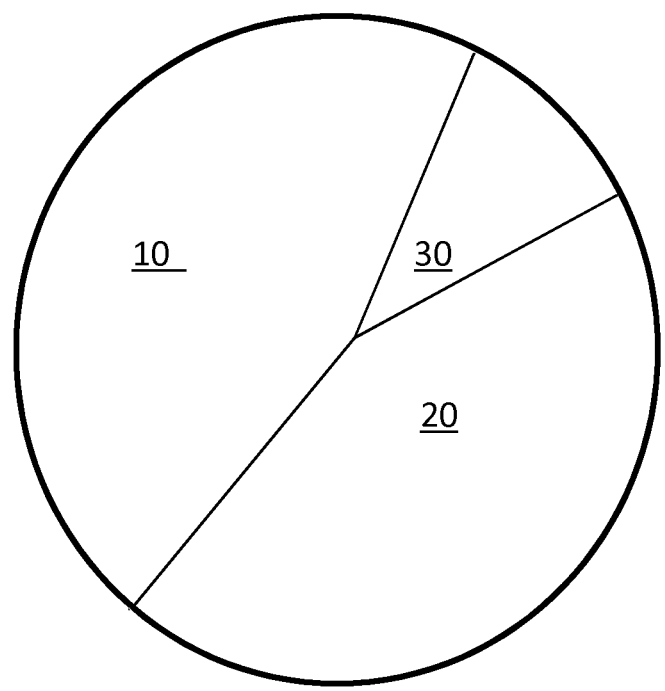

CANNA AND SHEA TOPICAL CREAM

CROSS-REFERENCE TO RELATED APPLICATIONS

This application claims priority of application No. 61/368,163 filed on Jul. 27, 2010 the contents of which are incorporated herein as if fully restated.

BACKGROUND OF THE INVENTION (1) Field of the Invention

The invention generally relates to topical creams used for pain relief. More particularly, the invention relates to the use of Shea butter, canna butter and other ingredients for use in the manufacture of topical cream used for pain relief.

(2) Description of the Related Art

In the related art many patients with muscular or joint pain symptoms are prescribed pain medicine delivered by injection or oral consumption. Topical ointments in the related art are often ineffective and counterproductive due to the presence of petroleum products and other non-organic ingredients. Thus, there is a shortfall in the related art and room for methods and articles of manufacture related to topical pain relief cream made with organic ingredients.

BRIEF SUMMARY OF THE INVENTION

The present invention overcomes shortfalls in the related art by presenting an unobvious and unique combination, configuration and processing of organic ingredients to create a topical cream having unexpected results in topical pain management.

One of the many advantages of the various embodiments of the invention is the ability of the disclosed article of manufacture to effectively diminish pain originating from joints, muscles and other areas of the body. Unlike the related art, no petroleum products or alcohol are used. The disclosed substance is applied topically and is thus ideal for patients who eschew needles or the oral consumption of medicine.

Another advantage of the various embodiments of the invention is the use of dried cannabis leafs, as opposed to cannabis buds or flowers. The use of dried cannabis leafs within the disclosed manufacturing process provides the necessary analgesic properties without need of using more costly cannabis buds or flowers.

The disclosed cream also delivers unexpected results in effectively treating dry skin, sunburn and other skin problems. The disclosed cream is typically applied directly over joints, muscles and other areas of pain.

The manufacture of one embodiment of the invention includes the production of canna butter and then the subsequent mixing of the manufactured canna butter with Shea butter a compound extracted from the African Shea tree. Optionally, lavender oil is used to enhance the smell of the product.

The manufacture of one embodiment of the disclosed canna butter involves the covering of dried cannabis leafs with conventional butter or cooking and then simmering for 7 to 12 hours. The remaining contents are then filtered.

An unexpected result of the disclosed article of manufacture is that the resulting cream contains UV radiation protective qualities and may be used as a topical sun screen.

These and other objects and advantages will be made apparent when considering the following detailed specification when taken in conjunction with the drawings.

BRIEF DESCRIPTION OF THE DRAWINGS

FIG. 1 is a pie diagram displaying the relative partitions of ingredients to manufacture one embodiment of the invention.

REFERENCE NUMERALS IN THE DRAWINGS

10 is a representation of Shea butter
20 is a representation of the disclosed canna butter
30 is a representation of scent oil, such as lavender oil

DETAILED DESCRIPTION OF EMBODIMENTS OF THE INVENTION

The following detailed description is directed to certain specific embodiments of the invention. However, the invention can be embodied in a multitude of different ways as defined and covered by the claims and their equivalents. In this description, reference is made to the drawings wherein like parts are designated with like numerals throughout.

Unless otherwise noted in this specification or in the claims, all of the terms used in the specification and the claims will have the meanings normally ascribed to these terms by workers in the art.

Unless the context clearly requires otherwise, throughout the description and the claims, the words "comprise," "comprising" and the like are to be construed in an inclusive sense as opposed to an exclusive or exhaustive sense; that is to say, in a sense of "including, but not limited to." Words using the singular or plural number also include the plural or singular number, respectively. Additionally, the words "herein," "above," "below," and words of similar import, when used in this application, shall refer to this application as a whole and not to any particular portions of this application.

The above detailed description of embodiments of the invention is not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize. For example, while steps are presented in a given order, alternative embodiments may perform routines having steps in a different order. The teachings of the invention provided herein can be applied to other systems, not only the systems described herein. The various embodiments described herein can be combined to provide further embodiments. These and other changes can be made to the invention in light of the detailed description.

Any and all the above references and U.S. patents and applications are incorporated herein by reference. Aspects of the invention can be modified, if necessary, to employ the systems, functions and concepts of the various patents and applications described above to provide yet further embodiments of the invention.

These and other changes can be made to the invention in light of the above detailed description. In general, the terms used in the following claims, should not be construed to limit the invention to the specific embodiments disclosed in the specification, unless the above detailed description explicitly defines such terms. Accordingly, the actual scope of the invention encompasses the disclosed embodiments and all equivalent ways of practicing or implementing the invention under the claims.

Referring to FIG. 1, a representation of one embodiment of the disclosed article of manufacture is shown in the form of a pie chart. Item 10, represents Shea butter and is in equal proportion to the disclosed canna butter 20. A smaller amount of scent oil, or scent substance may be added and is shown herein as 30. In the preferred embodiment, lavender oil is used to enhance the scent of the disclosed cream. In other embodiments the canna butter may comprise 40 to 60%, Shea butter 40 to 60% and scent oil 0 to 10%.

One embodiment of the disclosed canna butter may be manufactured as follows:

1. Melt conventional butter, such as cow butter, or heat olive or vegetable oil;
2. Pour melted butter or heated vegetable oil over dried cannabis leaves. The dried cannabis leaves need to be completely covered in either the melted butter or heated vegetable oil.
3. Cook, at a low simmer the covered dried cannabis leaves for approximately 10 to 12 hours.
4. Strain the remaining material with a filter, such as a cheese cloth or fine strainer, then cool for 30 to 60 minutes such that the cooled material may be mixed or blended with Shea butter.
5. Optionally, add a desired amount of lavender oil to the strained mixture and place the mixture into sterile glass containers.
6. The cooled mixture is now sometimes called canna butter.
7. The manufactured canna Shea butter is sometimes called "the disclosed cream" or canna and Shea topical cream or emollient.

In other embodiments, the use of other ingredients is contemplated, and such ingredients include petroleum jelly and alcohol.

Embodiments of the disclosed compositions and methods include, but are not limited to the following items.

Items

[Item 1] A method of manufacturing an ointment for pain relief, the method comprising the steps of:
a) melting conventional butter within a first container;
   b) placing dried cannabis leaves within a second container with the second container suitable for accepting heat;
   b) pouring the melted conventional butter within the first container upon the dried cannabis leaves contained within the second container, such that the cannabis leaves are completely covered by the melted conventional butter;
   c) for 8 to 12 hours, applying heat to the bottom of the second container, with the heat being within the range of 100 to 150 degrees Fahrenheit;
   d) filtering the remaining contents of the second container with a cloth filter;
   e) allowing the filtered contents of the second container to cool at a room temperature of between 60 and 90 degrees Fahrenheit; and
   f) creating an ending mixture by mixing together portions in the range of 40 to 60% of Shea butter and portions in the range of 40 to 60% of the contents of the second container.

[Item 2] The method of item 1 wherein the filtering of the contents of the second container occurs with a filter having pours in the range of 0.9 square mm and 2.6 square mm.

[Item 3] the method of item 2 wherein the ending mixture comprises a proportion of Shea butter is the range of 45 to 55% and the range of the material of the second container is in the range of 45 to 55%.

[Item 4] The method of item 3 wherein the ending mixture comprises a portion of lavender oil in the range of 1 to 5%, Shea butter in the range of 45 to 55% and contents of the second container in the range of 45 to 55%.

[Item 5] the method of item 1 wherein conventional butter is comprised of the cow butter, sheep butter, olive oil or vegetable oil.

[Item 6] The composition comprising the ending mixture of item 1.

[Item 7] The composition of item 6 used for protecting human skin from ultraviolet light.

[Item 8] The composition of item 6 used for topical pain relief.

The disclosed compositions have shown unexpected results in topical pain relief, smell, shelf life, use as sunscreen and skin moisturizer.

What is claimed is:

1. A method of manufacturing an ointment for pain relief, the method comprising the steps of:
   a) melting conventional butter within a first container;
   b) placing dried cannabis leaves within a second container with the second container suitable for accepting heat;
   b) pouring the melted conventional butter within the first container upon the dried cannabis leaves contained within the second container, such that the cannabis leaves are completely covered by the melted conventional butter;
   c) for 8 to 12 hours, applying heat to the bottom of the second container, with the heat being within the range of 100 to 150 degrees Fahrenheit;
   d) filtering the remaining contents of the second container with a cloth filter;
   e) allowing the filtered contents of the second container to cool at a room temperature of between 60 and 90 degrees Fahrenheit; and
   f) creating an ending mixture by mixing together portions in the range of 40 to 60% of Shea butter and portions in the range of 40 to 60% of the contents of the second container.

2. The method of claim 1 wherein the filtering of the contents of the second container occurs with a filter having pours in the range of 0.9 square mm and 2.6 square mm.

3. The method of claim 2 wherein the ending mixture comprises a proportion of shea butter is the range of 45 to 55% and the range of the material of the second container is in the range of 45 to 55%.

4. The method of claim 3 wherein the ending mixture comprises a portion of lavender oil in the range of 1 to 5%, Shea butter in the range of 45 to 55% and contents of the second container in the range of 45 to 55%.

5. The method of claim 1 wherein conventional butter is comprised of the cow butter, sheep butter, olive oil or vegetable oil.

6. The composition comprising the ending mixture of claim 1.

7. The composition of claim 6 used for protecting human skin from ultraviolet light.

8. The composition of claim 6 used for topical pain relief upon human skin.

* * * * *